United States Patent [19]

Hanifl et al.

[11] Patent Number: 5,378,226
[45] Date of Patent: Jan. 3, 1995

[54] SWAB IMPREGNATING AND DISPENSING SYSTEM

[75] Inventors: Paul H. Hanifl, Barrington Hills; Lawrence G. Ponsi, Wheeling; John Posey, McHenry, all of Ill.

[73] Assignee: Sage Products, Inc., Crystal Lake, Ill.

[21] Appl. No.: 64,590

[22] Filed: May 19, 1993

Related U.S. Application Data

[63] Continuation-in-part of Ser. No. 821,010, Jan. 15, 1992, abandoned.

[51] Int. Cl.$^6$ ............................................. A61M 35/00
[52] U.S. Cl. ............................................. 604/3; 604/1; 604/2; 604/49; 604/57; 604/56; 604/82; 604/87; 206/438; 206/570
[58] Field of Search ........................... 604/1-3, 604/49, 56-57, 82, 87-90, 408-409, 317-318, 322-324; 128/760, 763, 766, 767

[56] References Cited

U.S. PATENT DOCUMENTS

| | | | |
|---|---|---|---|
| 2,902,146 | 9/1959 | Doherty | 206/438 |
| 3,547,257 | 12/1970 | Armentrout | 206/439 |
| 3,835,834 | 9/1974 | Brown et al. | 604/1 |
| 3,938,658 | 2/1976 | Rohode | 206/439 |
| 4,206,843 | 6/1980 | Rainey | 604/3 |
| 4,211,323 | 7/1980 | Olsen | 604/3 |
| 4,747,719 | 5/1988 | Parkin | 604/3 |
| 4,813,432 | 3/1989 | Saint-Amand | 206/438 |

*Primary Examiner*—Randall L. Green
*Assistant Examiner*—P. Zuttarelli
*Attorney, Agent, or Firm*—Lee, Mann, Smith, McWilliams, Sweeney & Ohlson

[57] ABSTRACT

A system for impregnating and dispensing a swab. An outer bag is provided having at least one swab and a burst pouch located therein. The burst pouch is opened within the bag while the bag is sealed, impregnating the swab before its removal. The bag is then opened, and the impregnated swab is removed through an access opening in the bag. The access opening is located so that the bag may be lain horizontally without liquid in the bag spilling from the bag. The pouch is oriented in the bag to be in proximity to the absorbent head of the swab.

22 Claims, 2 Drawing Sheets

SWAB IMPREGNATING AND DISPENSING SYSTEM

RELATED APPLICATION

This application is a continuation-in-part of co-pending U.S. patent application Ser. No. 07/821,010, filed Jan. 15, 1992 abandoned.

BACKGROUND OF THE INVENTION

This invention relates to mouth care swabs, and in particular to a system for easily impregnating and dispensing one or more swabs requiring considerably less effort than previously and protecting the impregnating liquid from spilling from the bag containing the swab.

Mouth care swabs of the nature of the present application are designed for single use. Such a swab is depicted in United States Design Patent No. D 282,698, assigned to the assignee of the present application. A suction-type swab of the nature the invention is depicted in U.S. patent application Ser. No. 717,858, filed Jun. 19, 1991, now U.S. Pat. No. 5,085,633, the disclosure of which is incorporated herein by reference, and which is also owned by the assignee of the present application.

Swabs of the nature used with the present application are impregnated with a mouth care solution before treatment of a patient. In one form of use of such swabs, the swabs are provided in bulk, and are individually dipped into a container of mouth care solution before use. In another form of use of the swabs, one or more swabs are provided as a kit with a packet of solution. In order to use the swab, the packet is torn open, the swab is dipped into the packet, and is then used for oral care.

However the swabs have previously been used, the process of use is cumbersome. The swab must be physically dipped in a mouth care solution, whether that solution is located in a packet or in a larger container. As previously practiced, the process requires two hands, and the undesirable step of dipping a swab before its use.

SUMMARY OF THE INVENTION

The invention relates to a system for impregnating and dispensing a swab particularly used for mouth care. The system includes an outer, sealed bag which has at least one swab located therein. A burst pouch is disposed within the sealed bag, the pouch containing a mouth care solution for impregnating the swab. The pouch includes means for opening the pouch while the pouch is sealed within the bag in order to release the liquid within the sealed bag to impregnate the swab. Access means is provided on one side of the bag and spaced from the side edges of the bag for allowing removal of an impregnated swab from the bag while excess liquid remains in the bag without spilling therefrom.

In accordance with one form of the invention, the access means comprises a line of weakening in one wall of the bag on one side. Preferably, the line of weakening is either a perforation or a partial cutting of the bag. In another form of the invention, the access means comprises a slit through the one wall of the bag, with a release means sealing the slit. Preferably, the release means comprises a peel away tab which is removed to expose the slit.

In accordance with a preferred form of the invention, means is provided for metering liquid impregnating the swab. That means comprises sizing the access slit in the bag in relation to the absorbent head of the swab such that the slit squeezes excess liquid from the head as the swab is removed through the slit. Thus, only a predetermined and desired amount of mouth care solution is carried by the swab as it is removed from the bag.

The pouch is opened within the bag in order to impregnate the swab or swabs without requiring opening of the bag. In one form of the invention, the pouch is provided with an area of weakening so that pressure applied to the pouch will cause the solution to fracture the pouch in order to expel the liquid contents. In another form of the invention, means is provided to pierce the pouch while sealed within the bag. In accordance with this form of the invention, the means to pierce comprises a clip engaging the pouch and having a puncturing tip which, when pushed into the pouch, pierces the pouch to expel its contents. In yet another form of the invention, an excess quantity of air is entrapped within the pouch so that when the pouch is compressed, the entrapped air is compressed and fractures the pouch to release the entrained liquid.

BRIEF DESCRIPTION OF THE DRAWINGS

The invention is described in the following description of examples embodying the best mode of the invention, taken in conjunction with the drawing figures, in which.

DESCRIPTION OF EXAMPLES EMBODYING THE BEST MODE OF THE INVENTION

Figure 1:
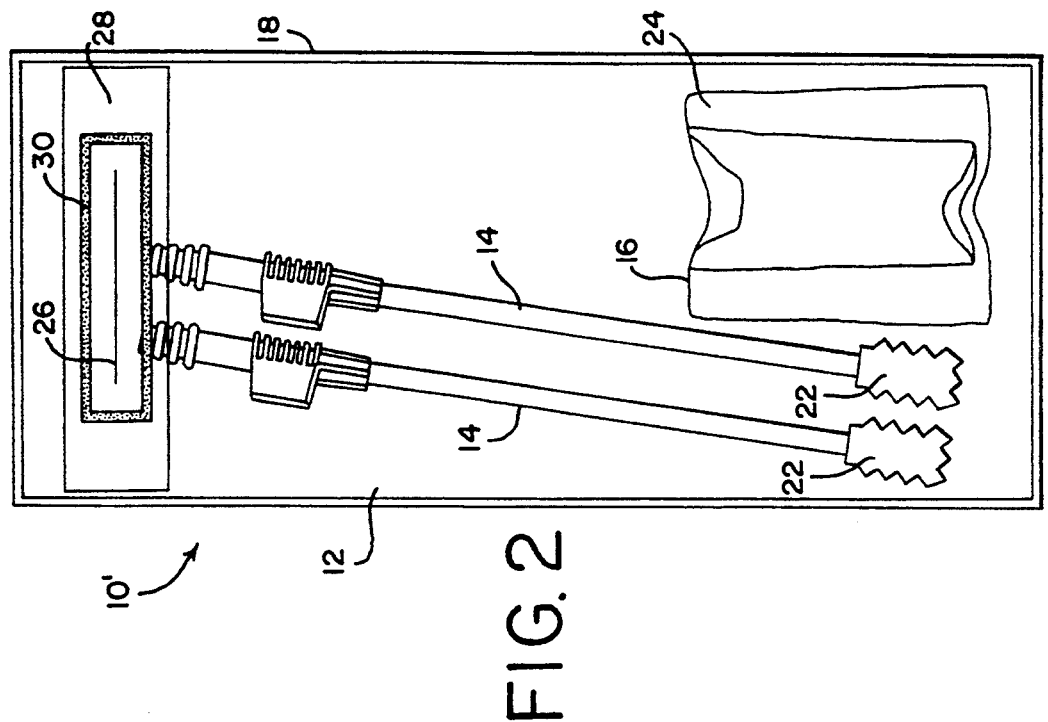
FIG. 1 is a schematic view of an impregnating and dispensing system according to the invention.

A system for impregnating and dispensing a swab is shown generally at 10 in the drawing figures. The system 10 is composed of three basic parts, a bag 12, one or more swabs 14, and a burst pouch 16.

The swabs 14 and burst pouch 16 are located within the bag 12. The bag 12 can be formed in a conventional fashion of two sheets of plastic, such as polyethylene, which are heat sealed together at a heat seal 18 about the periphery of the bag 12. Thus, the swabs 14 and pouch 16 are normally wholly sealed within the bag 12 during shipping and storage, and thus may be sterile.

The bag 12 also includes an access to the interior of the bag in the form of a perforation or line of weakening 20. As shown, the perforation 20 is spaced from the side edges of the bag 12 and is sized sufficiently so that the perforation 20 can be severed to remove the swabs 14 from the bag 12. The perforation 20 is spaced from the side edges of the bag 12 in order to help retain excess liquid within the bag 12 when one or both of the swabs 14 has been removed. Even with the bag 12 lying horizontally, the bag normally bows upwardly due to its contents, and with the perforation 20 on its upper side, liquid within the bag 12 normally remains contained within the bag. However, if the perforation 20 extended to one of the side edges of the bag 12 at the heat seals 18, liquid within the bag 12 would be considerably more susceptible to leaking from the bag since the heat sealed side edges normally would lie flatter on the surface upon which the bag 12 lies.

The swabs 14 are preferably as explained in incorporated U.S. Pat. No. 5,085,633. However, other types of swabs can be utilized so long as the swabs have an absorbent head 22 or similar absorbent area for impregnation with liquid contained within the burst pouch 16.

The burst pouch 16 preferably is formed of plastic, such as polyethylene, or a composite, multi-layer structure that is non-reactive to liquid mouth care solution contained within the pouch 16. The mouth care solution can be of many different forms, including a mint flavored hydrogen peroxide solution sold by Sage Products of Crystal Lake, Ill. under the trademark "PEROX-A-MINT".

The pouch 16 can be formed in a conventional fashion of a folded over length of material that is heat sealed at 24 along three edges to form the pouch, with a sufficient quantity of mouth care solution being located therein. In the pouch 16 illustrated in FIG. 1, it is preferred that the pouch also be inflated with an excess of air in the pouch 16 so that the pouch 16 may be burst by applying pressure to the pouch, compressing the air therewithin until either the structure of the pouch 16 ruptures, or one of the heat seals 24 fractures. However the pouch 16 opens, the liquid mouth care solution contained therewithin then is free to saturate the absorbent heads 22 of the swabs 14.

Figure 2:
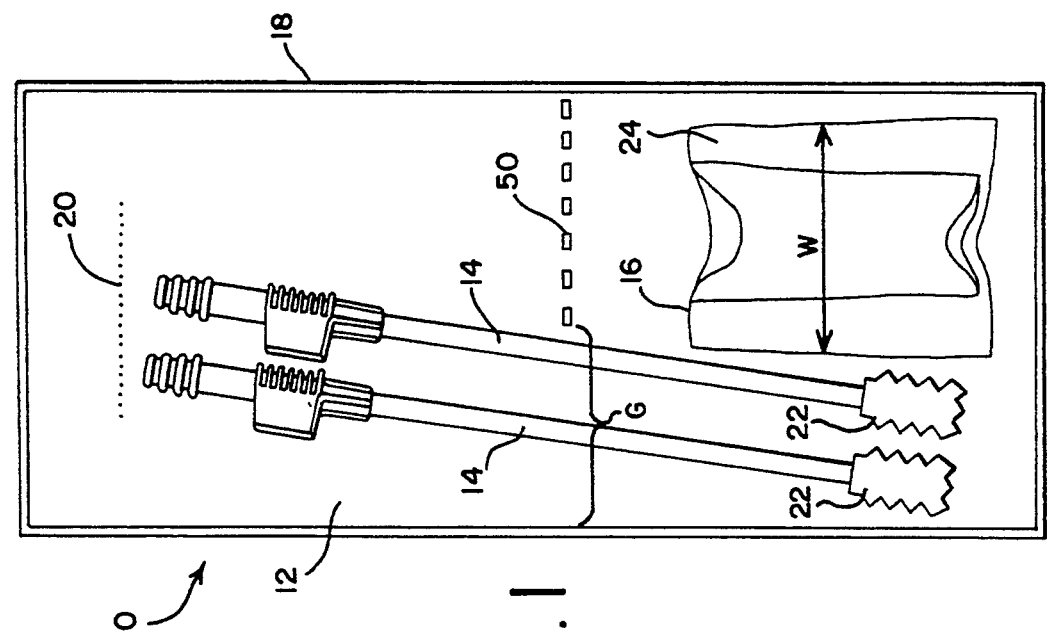
FIG. 2 is a schematic view of a second form of the invention, with a peel away tab sealing an access opening to the bag.

The form 10' of the invention shown in FIG. 2 is identical to that of FIG. 1, except that the line of perforation 20 of FIG. 1 has been replaced by a slit 26 in the wall of the bag 12. For sealing purposes, the slit 26 is overlain by a peel away tab 28 which is sealed by a heat seal 30 to the bag 12. The user, by grasping the tab 28, can peel the tab 28 to sever the heat seal 30, thus exposing the slit 26 for removal of the swabs 14 in the same fashion as illustrated in FIG. 1. The system 10' of FIG. 2 is used in the same fashion as the system 10 of FIG. 1.

Figure 3:
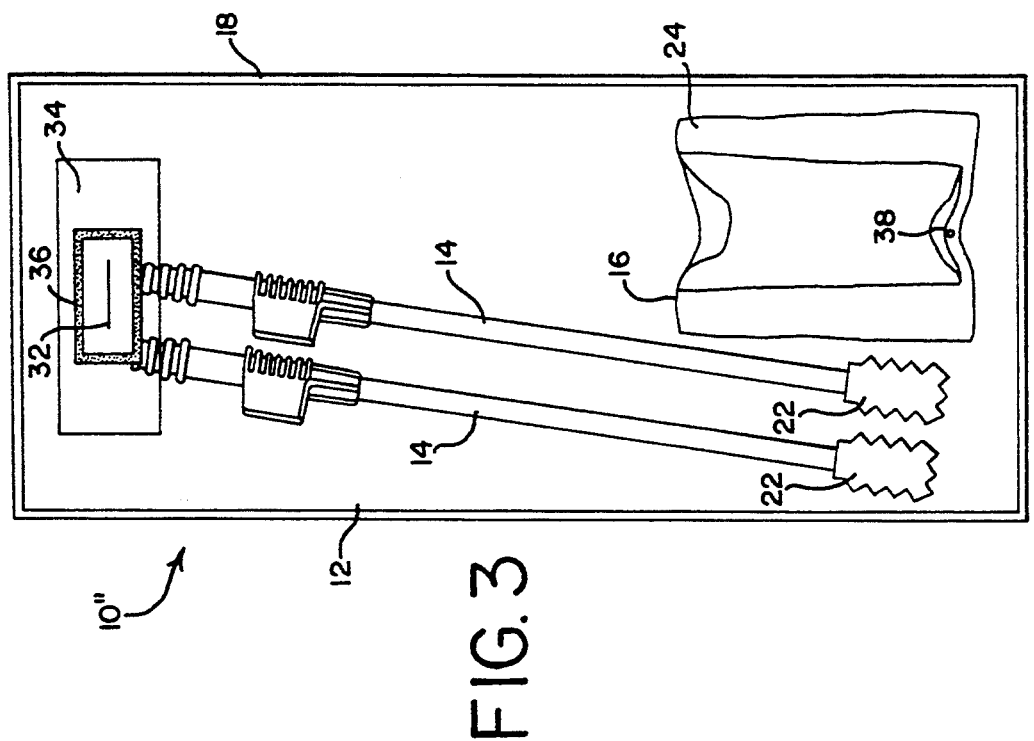
FIG. 3 is a schematic view of yet another form of the invention, similar to that of FIG. 2, but having the access opening reduced in size for metering purposes.

Turning next to FIG. 3, the system 10" illustrated is essentially similar to that shown in FIG. 2, in that the bag 12 includes a slit 32 overlain by a peel away tab 34 which is heat sealed to the bag 12 by a heat seal 36. In this form of the invention, however, the slit 32 is considerably smaller in size than the slit 26. The slit 32 provides metering of liquid impregnating the swabs 14 as the swabs are removed from the bag 12. The slit 32 is formed in size relative to the size of the head 22 such that, as the swab 14 is removed from the bag 12 through the slit 32, the slit 32 squeezes excess liquid from the head 22. Thus, the slit 32 is used to meter and control the amount of liquid impregnating the swab 14.

The pouch 16 illustrated in FIG. 3 is identical to that shown in FIGS. 1 and 2, except that the pouch 16 also includes a perforation 38 extending through the heat seal 24. As illustrated, the perforation 38 is located quite close to the contents of the pouch 16 so that when pressure is applied to the pouch 16, the pouch will fracture or burst at the perforation 38. The perforation 38 therefore facilitates the dispensing of the liquid contents of the pouch 16 within the bag 12. The perforation 38 is also situated so that when the pouch fractures, it will direct its liquid contents toward the swab heads 22.

Figure 4:
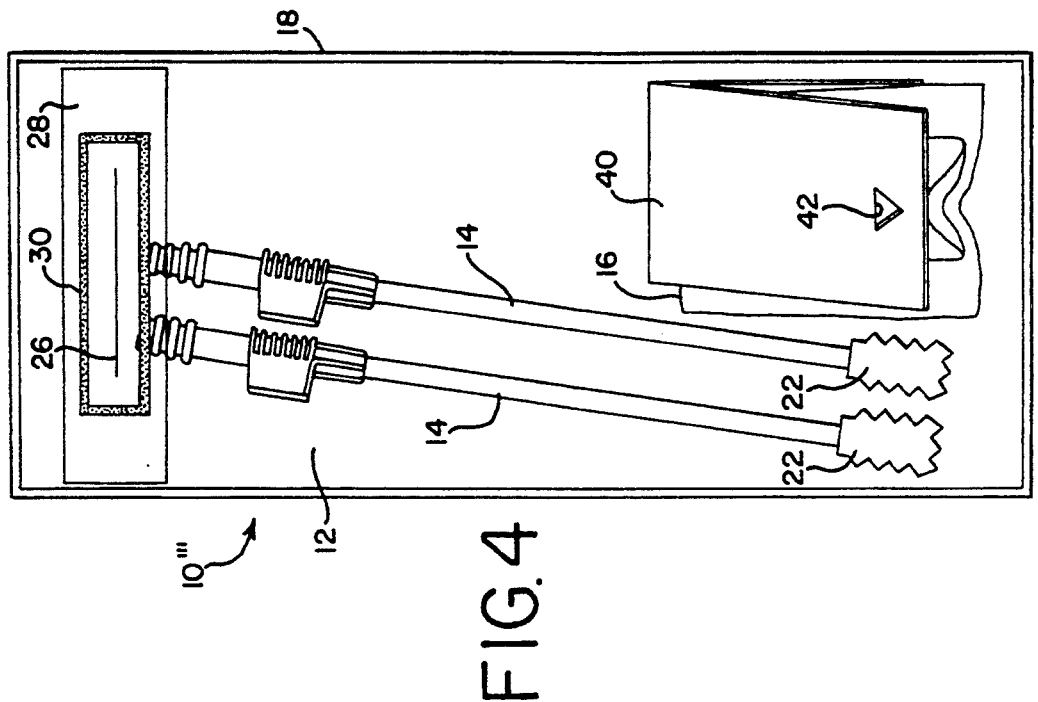
FIG. 4 is a schematic view of the invention, similar to that illustrated in FIG. 2, but with a pouch-piercing clip being incorporated for piercing of the liquid-containing pouch.

The final form of the system 10'" shown in FIG. 4 is essentially similar to that illustrated in FIG. 2, except that a clip 40 is provided engaging the pouch 16. The clip 40 may be made of substantially rigid metal or plastic, and includes a puncturing tip 42 aimed toward the pouch 16. Squeezing of the clip 40 causes the puncturing tip 42 to pierce the pouch 16, releasing the liquid contents of the pouch into the bag 12. Again, the tip 42 is oriented so that when the pouch fractures, the liquid contents of the pouch will be directed toward the swab heads 22.

In use, a sealed bag 12 is shipped in the forms illustrated in FIGS. 1–4, and when the swabs 14 are to be used, the pouch 16 is burst within the bag 12, releasing its liquid contents to impregnate the absorbent heads 22 of the swabs 14. In all forms of the invention, pressure must be applied to the pouch 16, either to cause the pouch to fracture due to contained air, fracture due to a perforation 38, or fracture due to the puncturing tip 42 of the clip 40. Once the pouch 16 has been fractured, the liquid contents impregnate the swab 14, and the bag 12 is then opened. In the form shown in FIG. 1, the bag is stretched until the perforation line 20 severs. In the remaining forms of the invention, the peel away tabs 28 or 34 are removed to expose the respective slits 26 or 32. Finally, one or both of the swabs 14 is removed through the opening in the bag 12.

In the form shown in FIG. 3, as the swab 14 is removed, the slit 32 engages and squeezes the head 22 of a swab 14 as it is removed, removing excess liquid, and therefore metering the amount of liquid that is contained in the head 22 as the swab 14 is removed from the bag 12.

In all forms of the invention, it is important that the perforation 20 or slits 26 or 32 be spaced from the side edges of the bag 12. As explained above, spacing of the access opening from the side edges of the bag 12 permits the bag 12 to hold a sufficient quantity of liquid mouth care solution dispensed by the pouch 12 without leaking from the bag 12, even when the bag is prone, so long as the opening is on top of the bag 12 as it lies prone. A saturated swab can therefore be withdrawn from the bag 12 without spilling of the remaining liquid contents within the bag 12.

It is preferred that the burst pouch 16 be retained within the bag 12 in proximity to the absorbent heads 22 of the swabs 14, so that when the pouch is burst, the absorbent heads are immediately impregnated with the solution within the burst pouch. To this end, as shown in FIG. 1, the bag 12 includes a heat seal 50 extending across the bag intermediate the opposite ends of the bag. The heat seal may be a continuous heat seal, or may, as illustrated, be a series of spaced seals forming the heat seal. In any event, the heat seal 50 is formed between the front and rear films forming the bag 12, and is located so that the pouch 16 is oriented in the bottom of the bag 12 proximate the absorbent heads 22 of the swabs 14.

The pouch 16 has a given width W, as illustrated in FIG. 1. In order to assure that the pouch 16 remains in the bottom of the bag 12 proximate the absorbent heads 22, the barrier 50 needs to extend across the width of the bag 12 sufficiently to prevent the pouch 16 from bypassing the barrier 50. Thus, the barrier 50 extends sufficiently so that there is a gap G formed in the barrier 50, the width of the gap G being no greater than the given width W of the burst pouch 16. Thus, even if the bag 12 is handled roughly during transporting, the burst pouch 16 will always be retained by the heat seal 50 in the bottom of the bag 12 proximate the absorbent heads 22. Therefore, when the burst pouch 16 is fractured, the solution contained within the burst pouch will immediately impregnate the absorbent heads 22, without the need for either reorienting the burst pouch 16 before its fracture, or the necessity of manually guiding the pouch fluid within the bag 12 to impregnate the heads 22 if the pouch 16 is burst within the bag 12 at a location widely spaced from the heads 22.

Although the partial barrier in the form of the heat seal 50 has been illustrated only in FIG. 1, it will be evident that the same barrier will be employed in the embodiments of FIGS. 2-4. In all embodiments, a sufficient gap G must remain to allow the swabs 14 to be withdrawn therethrough, and also prevent the pouch 16 from passing past the heat seal 50.

Various changes can be made to the invention without departing from the spirit thereof or scope of the following claims.

What is claimed is:

1. A system for impregnating and dispensing a swab, comprising
   a. an outer, sealed bag having at least one swab located therein, said bag comprising opposite, generally flat, flexible sides sealed along side edges and end edges thereof,
   b. a frangible pouch disposed within said sealed bag, said pouch containing a liquid and including means for opening said pouch while sealed within said bag for releasing said liquid within said sealed bag to impregnate said swab so that said swab becomes an impregnated swab, and
   c. access means on one side of said bag extending laterally across a portion of said one side and being spaced from the side edges and end edges of said bag for allowing removal of an impregnated swab from said bag while excess liquid remains within said bag.

2. A system according to claim 1 in which said means for opening comprises an area of weakening in said pouch.

3. A system according to claim 1 in which said means for opening comprises an excess quantity of entrapped air within said pouch such that compression of said pouch causes the entrapped air to fracture said pouch to release said liquid.

4. A system according to claim 1 in which said access means comprises a line of weakening in one wall of said bag on said one side.

5. A system according to claim 4 in which said line of weakening is perforated.

6. A system according to claim 1 in which said access means comprises a slit in one wall of said bag on said one side, and including release means sealing said slit.

7. A system according to claim 6 in which said release means comprises a peel away tab.

8. A system according to claim 1 in which said means for opening comprises means to pierce said pouch while seated within said bag.

9. A system according to claim 8 in which said means to pierce comprises a clip engaging said pouch and having a puncturing tip.

10. A system according to claim 1 including means for metering liquid impregnating said swab.

11. A system according to claim 10 in which said access means comprises a slit and said swab includes an absorbent head, and said metering means comprises sizing of said slit relative to said absorbent head such that said slit squeezes excess liquid from said head as said swab is removed through said slit.

12. A system according to claim 11 including a peel away tab releasably sealing said slit.

13. A system according to claim 1 including means for orienting said pouch within said sealed bag.

14. A system according to claim 13 in which said swab includes an absorbent head, and in which said means for orienting comprises means for retaining said pouch proximate said head.

15. A system according to claim 14 in which said pouch has a given width, and in which said means for retaining comprises a partial barrier formed in said bag intermediate opposite ends of said bag, said barrier having a gap for passage of said swab therethrough, said gap having a width dimension not greater than said given width.

16. A system according to claim 15 in which said barrier comprises a heat seal in front and rear films forming said bag.

17. A method of impregnating and dispensing a swab located in combination with a liquid-filled frangible pouch in a sealed outer flexible bag comprising opposite sides and ends sealed along respective side and end edges thereof, the bag having an access location on one side located intermediate the side and end edges and extending laterally across a portion of said one side intermediate the side and end edges for allowing removal of the swab, comprising the steps of
   a. opening the pouch within the sealed outer bag to release the liquid from the pouch,
   b. impregnating the swab with liquid released within the sealed bag,
   c. opening the bag at the access location to form a dispensing slit in one wall of the bag intermediate the side edges of the bag, forming a reservoir in the bag when the bag lies on a side opposite said one side, and
   d. removing the swab through the dispensing slit.

18. A method according to claim 17 in which method step "a" includes applying pressure to the pouch to cause the liquid within the pouch to fracture the pouch to release the liquid.

19. A method according to claim 17 in which means is provided to pierce said pouch while sealed within said bag, and method step "a" includes using the pierce means to fracture the pouch to release the liquid.

20. A method according to claim 17 in which the access location includes a line of weakening, and method step "c" includes stretching the bag at the line of weakening to form the slit in the bag by severing the bag along the line of weakening.

21. A method according to claim 17 in which the slit is preformed in the bag and is overlain by a peel away tab sealing the slit, and method step "c" includes removing the peel away tab to expose the slit.

22. A method according to claim 17 in which the swab includes an absorbent head and the slit is sized relative to the head such that the slit engages the head as the swab is removed through the slit, and method step "d" includes using the slit to squeeze excess liquid from the head as the swab is removed through the slit.

* * * * *